United States Patent
Cooper

(10) Patent No.: US 10,246,016 B2
(45) Date of Patent: Apr. 2, 2019

(54) OPTICAL SURFACE CLEARING ARRANGEMENT

(76) Inventor: Joseph Richard Cooper, Sugar Valley, GA (US)

(*) Notice: Subject to any disclaimer, the term of this patent is extended or adjusted under 35 U.S.C. 154(b) by 552 days.

(21) Appl. No.: 11/602,167

(22) Filed: Nov. 20, 2006

(65) Prior Publication Data

US 2007/0103780 A1 May 10, 2007

Related U.S. Application Data

(63) Continuation-in-part of application No. 11/240,953, filed on Sep. 30, 2005, now Pat. No. 7,140,740.

(51) Int. Cl.
| | | |
|---|---|---|
| B60R 1/06 | (2006.01) | |
| G02B 27/00 | (2006.01) | |
| G01N 21/15 | (2006.01) | |

(52) U.S. Cl.
CPC ............ B60R 1/0602 (2013.01); *G01N 21/15* (2013.01); *G02B 27/0006* (2013.01)

(58) Field of Classification Search
CPC .......... B60R 1/0602; B60R 2001/1253; G02B 27/0006; G01N 21/15; G01N 2021/151
USPC .... 359/509, 507; 15/301, 312.1, 312.2, 313, 15/314, 316.1, 250.001, 250.01, 251.01, 15/250.02, 250.003
See application file for complete search history.

(56) References Cited

U.S. PATENT DOCUMENTS

| | | | | | |
|---|---|---|---|---|---|
| 1,717,904 | A | * | 6/1929 | Abernethy | 454/93 |
| 2,320,636 | A | * | 6/1943 | Miller | F16L 41/14 285/208 |
| 3,295,004 | A | * | 12/1966 | Hirsch | 313/110 |
| 3,469,088 | A | * | 9/1969 | Coleman et al. | 239/284.2 |
| 4,088,358 | A | * | 5/1978 | Hirsch | 239/284.2 |
| 4,505,001 | A | * | 3/1985 | Fasolino | 15/250.002 |
| 4,561,732 | A | * | 12/1985 | Japes | 359/509 |
| 5,096,287 | A | * | 3/1992 | Kakinami et al. | 352/132 |

(Continued)

FOREIGN PATENT DOCUMENTS

| | | | | |
|---|---|---|---|---|
| DE | 2411547 | A | * | 9/1975 |
| DE | 3721370 | A1 | * | 1/1988 |

(Continued)

*Primary Examiner* — Kristina M Deherrera
(74) *Attorney, Agent, or Firm* — Gardner Groff Greenwald & Villanueva PC

(57) ABSTRACT

A vehicle side-view mirror water removal arrangement is easily retrofitted to vehicles having an existing source of compressed air and a side-view mirror with a reflective surface. The arrangement includes a valve having an input port connected to the existing source of compressed air and an output port, the valve being movable between open and closed positions to control the flow of compressed air from the existing source of compressed air to the output port of the valve. A conduit's proximal end is connected to the output port of the valve with its distal end located at the side-view mirror for conducting the compressed air from the output port of the valve to the side-view mirror. A fastener fastens the distal end of the conduit to the side-view mirror so that the compressed air flows down the reflective surface of the side-view mirror, a nozzle at the distal end being provided to spread the compressed air substantially over an entire width of the side-view mirror to clear any water adhering to the reflective surface of the mirror.

20 Claims, 5 Drawing Sheets

(56) References Cited

U.S. PATENT DOCUMENTS

| | | | |
|---|---|---|---|
| 5,140,719 A * | 8/1992 | Cowan | 15/313 |
| 5,419,005 A * | 5/1995 | Mori | 15/313 |
| 5,546,630 A * | 8/1996 | Long | 15/313 |
| 5,708,859 A * | 1/1998 | Tajima et al. | 396/25 |
| 5,987,216 A * | 11/1999 | Krug | 392/379 |
| 6,077,361 A * | 6/2000 | Glenn | 134/21 |
| 6,249,931 B1 * | 6/2001 | Sato | 15/313 |
| 6,290,361 B1 * | 9/2001 | Berzin | 359/507 |
| 6,527,000 B1 * | 3/2003 | Randmae et al. | 134/99.1 |
| 6,527,871 B1 * | 3/2003 | Hanson et al. | 134/37 |
| 6,944,908 B2 * | 9/2005 | Hoetzer et al. | 15/316.1 |
| 7,140,740 B1 * | 11/2006 | Cooper | 359/509 |
| 2003/0155001 A1 * | 8/2003 | Hoetzer | B60S 1/0822 134/37 |
| 2006/0193049 A1 * | 8/2006 | Chen et al. | 359/509 |
| 2007/0183039 A1 * | 8/2007 | Irvin | 359/507 |
| 2007/0273971 A1 * | 11/2007 | Waldmann et al. | 359/509 |

FOREIGN PATENT DOCUMENTS

| | | |
|---|---|---|
| JP | 56008739 A * | 1/1981 |
| JP | 56163931 A * | 12/1981 |
| JP | 02310147 A * | 12/1990 |
| JP | 03235743 A * | 10/1991 |
| JP | 06171473 A * | 6/1994 |
| WO | WO 8800142 A1 * | 1/1988 |
| WO | WO 2005039932 A2 * | 5/2005 |

* cited by examiner

OPTICAL SURFACE CLEARING ARRANGEMENT

This is a Continuation-in-Part Application of U.S. patent application Ser. No. 11/240,953 filed Sep. 30, 2005 now U.S. Pat. No. 7,140,740.

BACKGROUND OF THE INVENTION

1. Field of the Invention

The present invention generally relates to an arrangement for clearing an optical surface of unwanted moisture and/or water adhering to and obscuring the surface, and more particularly, to such an arrangement where the optical surface is positioned remotely and generally out of reach.

2. Background of the Invention

Optical surfaces, such as, windows, transparent camera coverings, camera lenses, mirrors and the like, are oftentimes placed in locations not readily accessible for clearing. For example, on large trucks and buses, side-view mirrors and rear windows provide the only effective means for the driver to observe traffic to the rear of the vehicle, but they are difficult to reach for clearing while driving.

This is a problem when driving in inclement weather, because precipitation and moisture from the road can adhere to and obscure these optical surfaces making it difficult to see. Also, side-view mirrors and rear windows of buses are located high off of the ground, making it difficult to clean them when stopped. Moreover, during wet and rainy weather, the mirrors and rear windows need to be cleaned often so stopping to repeatedly wipe them is practical.

The use of cameras on vehicles is more prevalent now that video technology has become more affordable. For example, in addition to trucks, public transportation as well as school buses, and rental car shuttles routinely use cameras to obtain a rearward view to monitor the area behind the vehicle to make sure it is clear. These cameras can also be movable mounted so that the view can be selected and used as a surveillance camera inside or outside of the vehicle. Cameras exposed to the elements often have transparent covers to protect the camera lens from damage. During inclement weather, these covers or the camera lens itself can become covered with precipitation, water and moisture making it difficult to get a unclouded picture from the camera.

Similarly, security camera located outside are exposed to weather and over time, either the lens or transparent covering for the lens becomes soiled, making it difficult to get a clear picture. In addition, security cameras are often located at positions that are difficult to reach, such as, high on a pole or on a roof top of a building as well as inside the building on the ceiling or at an elevated position. This positioning makes it difficult for the camera lens or transparent cover to be reached for clearing.

In addition to the foregoing, optical surfaces associated with vehicle mirrors and cameras as well as security cameras are often moveable, making it even more difficult to clear effectively with an in situ device located at the optical surface because the optical surface do not stay in the same position.

There are known arrangements for clearing and clearing optical surfaces that use high velocity air flow, however, these known devices are expensive because they generally use a clearing solution in conjunction with the high velocity air flow and are inefficient since the air flow is directed upward over the optical surface and counter to the pull of gravity.

For example, U.S. Pat. Nos. 4,134,612 and 4,196,930 respectively disclose vehicle mirror clearing devices which use air flow deflectors to direct a stream of air across the face of the mirror and provide a clearing effect but these arrangements are generally ineffective since the force of the stream of air is limited by the vehicle's speed.

Accordingly, there is a need for a means by which remotely located, optical surfaces that are not easily accessible, such as, the back windows of buses, side-view mirrors of buses and trucks, cameras on large vehicles as well as security cameras located outside as well inside of buildings, can be easily and effectively cleared of grime and dirt as well as precipitation in a quick, easy, inexpensive and effective manner without the need for a person to reach the location of the optical surface and repeatedly manually wipe the surface to clear it of obscuring water droplets, moisture and/or precipitation on the optical surface.

SUMMARY OF THE INVENTION

Accordingly, it is an object of the present invention to provide a new and useful arrangement for clearing remotely positioned optical surfaces in hard to reach locations which overcomes the deficiencies of the prior art.

Another object of the present invention is to provide an optical surface clearing device which is easily retrofitted to vehicle or security camera arrangements without the need for expensive adaptations and the like.

Yet another object of the present invention is to provide an optical surface clearing device that is located at the inaccessible optical surface and operated remotely or automatically without the need for a person to manually clean the surface.

Still another object of the present invention is to provide an optical surface clearing device that issues a downwardly directed sheet of compressed air from a nozzle attached to the top portion of the optical surface substantially over the entire width of the surface to blow off any moisture or water adhering to the optical surface.

One particular advantageous feature of the present invention is that the nozzle of the optical surface clearing device is attached to the optical surface so that the device is effective even if the optical surface is moveable, as is the case, for example, with side-view mirrors and security cameras or the like.

Yet another advantageous feature of the present invention is that it is simple in construction than known arrangements and therefore, more reliable and less costly to manufacture as well as operate.

These and other objects, advantages, and features of the present invention are achieved by a device for clearing a remotely located optical surface of water and/or moisture, which according to one embodiment of the present invention comprises an air source for providing a blast of pressurized air; a nozzle positioned on the optical surface for spreading the blast of pressurized air onto the optical surface in a substantially downward direction; and control means for triggering the air source to provide the blast of pressurized air to the nozzle. The blast of pressurized air is spread substantially by the nozzle onto substantially the entire width of the optical surface to remove any obstructive material on the optical surface.

DETAILED DESCRIPTION OF THE PREFERRED EMBODIMENT(S)

Figure 1:
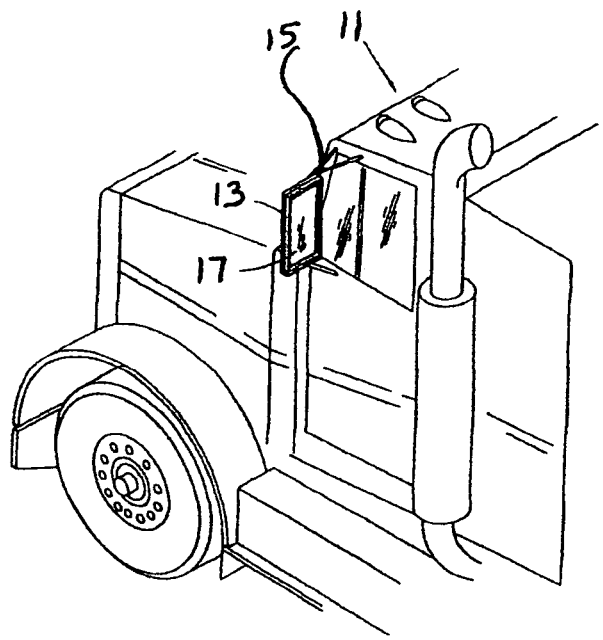
FIGS. 1 and 2 are perspective views of large-vehicle, side-view mirrors separate from the vehicle body and respectively located on the driver side and the passenger side of the vehicle in accordance with the prior art.
Figure 2:
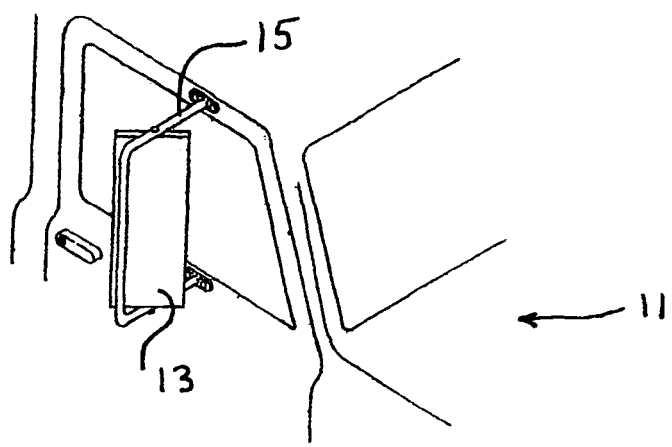
Figure 3:
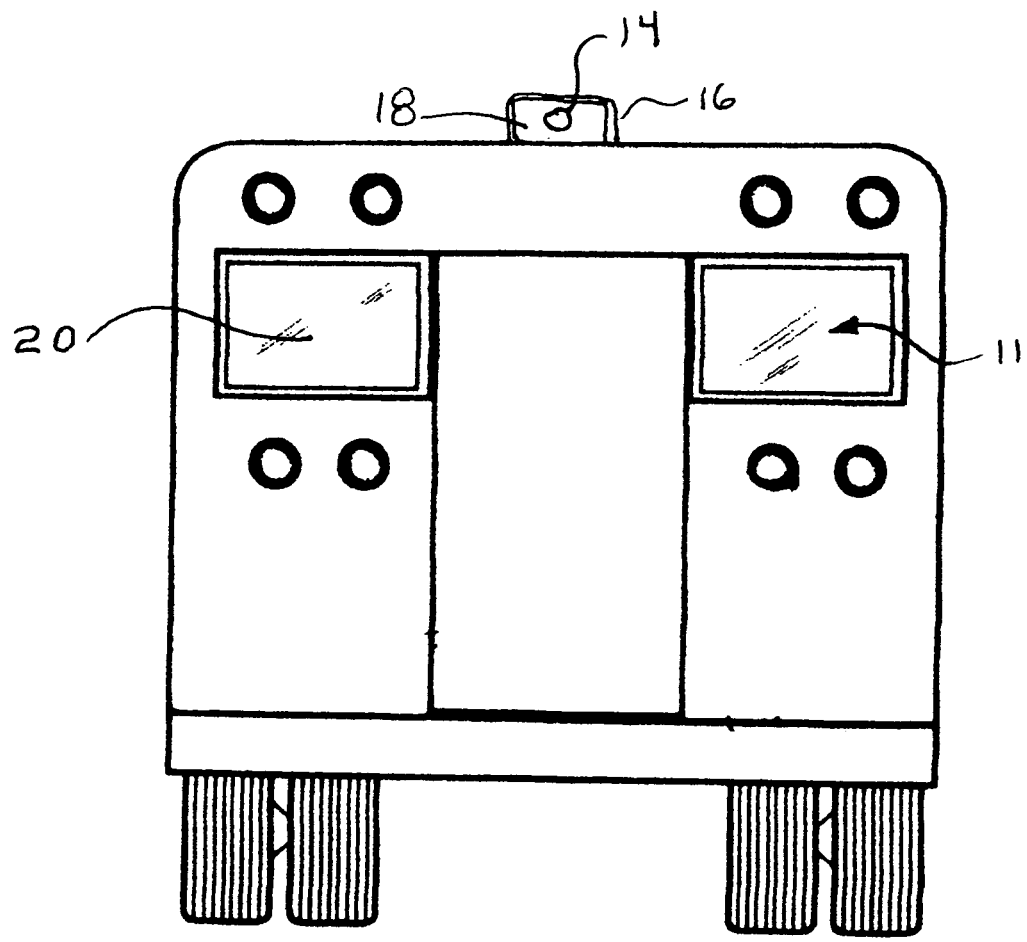
FIG. 3 is a rear planar view of a large vehicle, such as a school bus, having a camera for monitoring an obscured rear-view of the vehicle.

Referring to FIGS. 1 and 2, a large vehicle, generally indicated at 11, such as, for example, a school bus, truck, public or commercial transportation bus or the like, is shown having an optical surface, for example, the reflective surfaces 17 of side view mirrors 13 mounted in positions outwardly of the side of the vehicle 11 on supports 15 that are not easily reached. FIG. 3 similarly illustrates a large vehicle 11, for example, a school bus, having optical surfaces, for example, a transparent rear window 20 and a lens 14 or transparent lens cover 18 for the lens of camera 16 for monitoring the area behind the vehicle 11. The camera 16 can be movably mounted and used as a surveillance camera too, As a result of these arrangements, the optical surfaces of the side view mirrors 13, window 20 and the vehicle mounted camera 16 are exposed to the elements and prone to the accumulation of precipitation, water and/or road spray which obscure the optical surfaces resulting in a cloudy or unclear image. This is particularly true during inclement weather when road spray as well as precipitation adhere to the optical surfaces making it difficult get a clear image.

Figure 4:
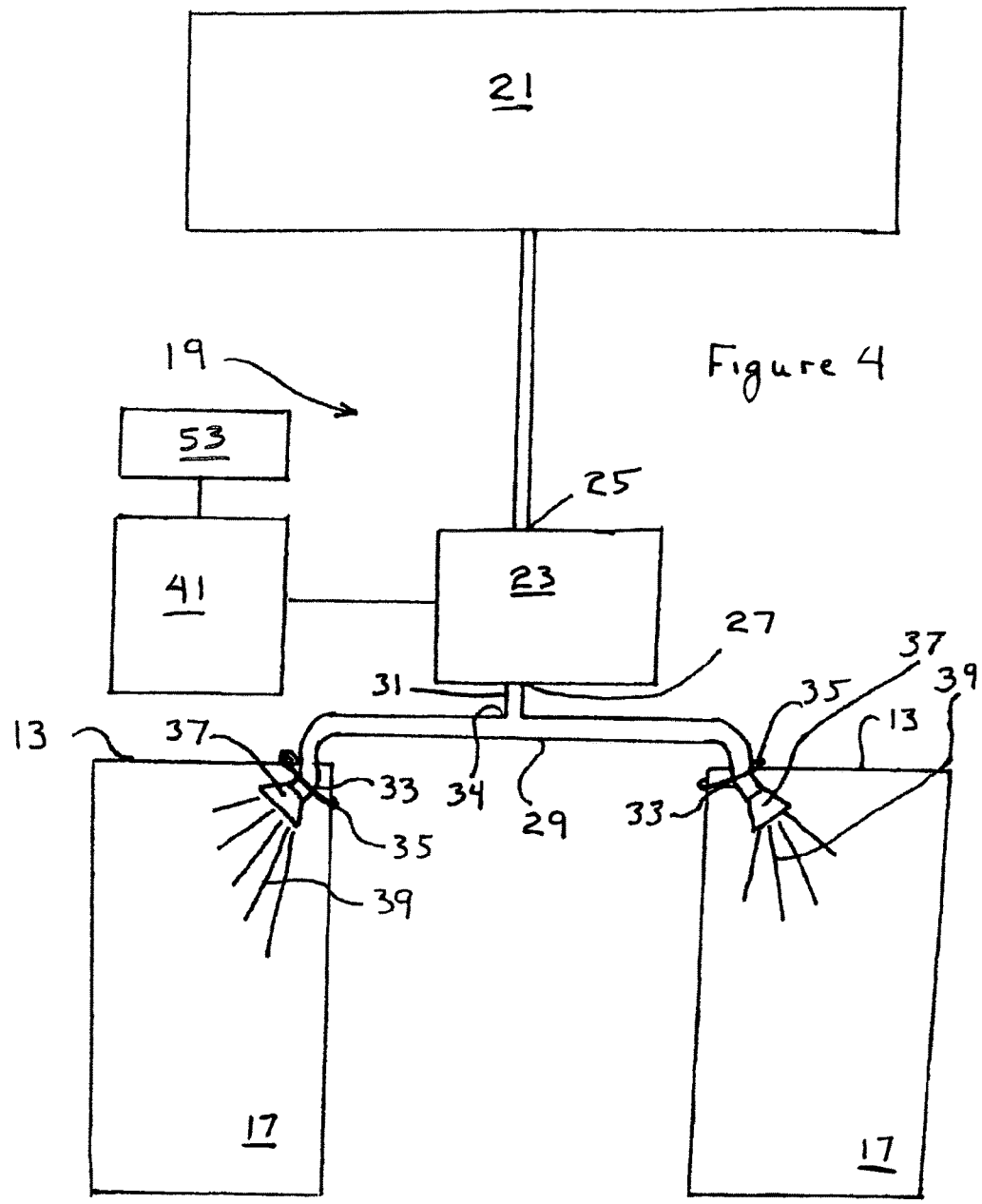
FIG. 4 is block diagram illustrating the components of one embodiment of the device of the present invention as applied an optical surface.

Referring to FIG. 4, a block diagram illustrates one embodiment of a device of the present invention, generally shown at 19, for clearing an optical surface which is not easily accessible. According to the embodiment of FIG. 4, the device 19 is adapted for use with or without an existing, on-board source of compressed air 21, i.e., if an on-board source of compressed air is not available, according to one embodiment of the present invention, an independent source of compressed air is provided. A valve 23 is provided for controlling the issuance of a blast of pressurized air from the compressed air source 21 and has an input port 25 connected to the compressed air source 21 and an output port 27. The valve 23 is movable between open and closed positions to control the issuance of blast of pressurized air from the air source 21 the output port 27 of the valve 23.

A conduit 29 has a proximal end 31 connected to the output port 27 of the valve 23 and a distal end 33 located at the optical surface, for example, the window 20, the reflective surface 17 of the side-view mirror 13 or lens 14 or transparent lens cover 18 of camera 16. The conduit is preferably made of a flexible material and by way of example may be comprised of plastic or elastomeric materials, noting however, that metallic materials are also within the scope of permissible conduit materials. In the embodiment shown in FIG. 4, a t-connector 34, by way of example, is employed so that the conduit 29 conducts the blasted of pressurized air from the output port 27 of the valve 23 to a plurality of optical surfaces on the vehicle although it is understood that the present invention is applicable to a single optical surface too.

A fastener 35 is also provided for fastening the distal end 33 of the conduit 29 at the optical surface, for example, at the reflective surface 17 of the side-view mirror 13. This is particularly important if the optical surface is movable so that the distal end 33 always state in the same relative position to the optical surface even if the optical surface is moved so that the blast 39 of pressurized air issued via a spreading nozzle 37 positioned on the distal end 33, is directed at and flows down over the optical surface, i.e., the reflective surface 17 of the side-view mirror. The fastener 35 comprises for example glue as well as other known mechanical fasteners such as ties and the like, however, glue is preferred because it permits the accurate positioning of the distal end 33 of the conduit 29 at the optical surface 17 of the side-view mirror 13.

The device 19 also includes a switching mechanism 41 for opening and closing the valve 23 to provide the blast 39 of compressed air from the compressed air source 21 to the distal ends 33 of the conduit 29. As more fully discussed below, the switching mechanism comprises a toggle switch manually operated by the driver to provide the blast of air or automatically operated when the windshield wipers of the vehicle are turned on or a combination of both manual and automatic.

Figure 5:
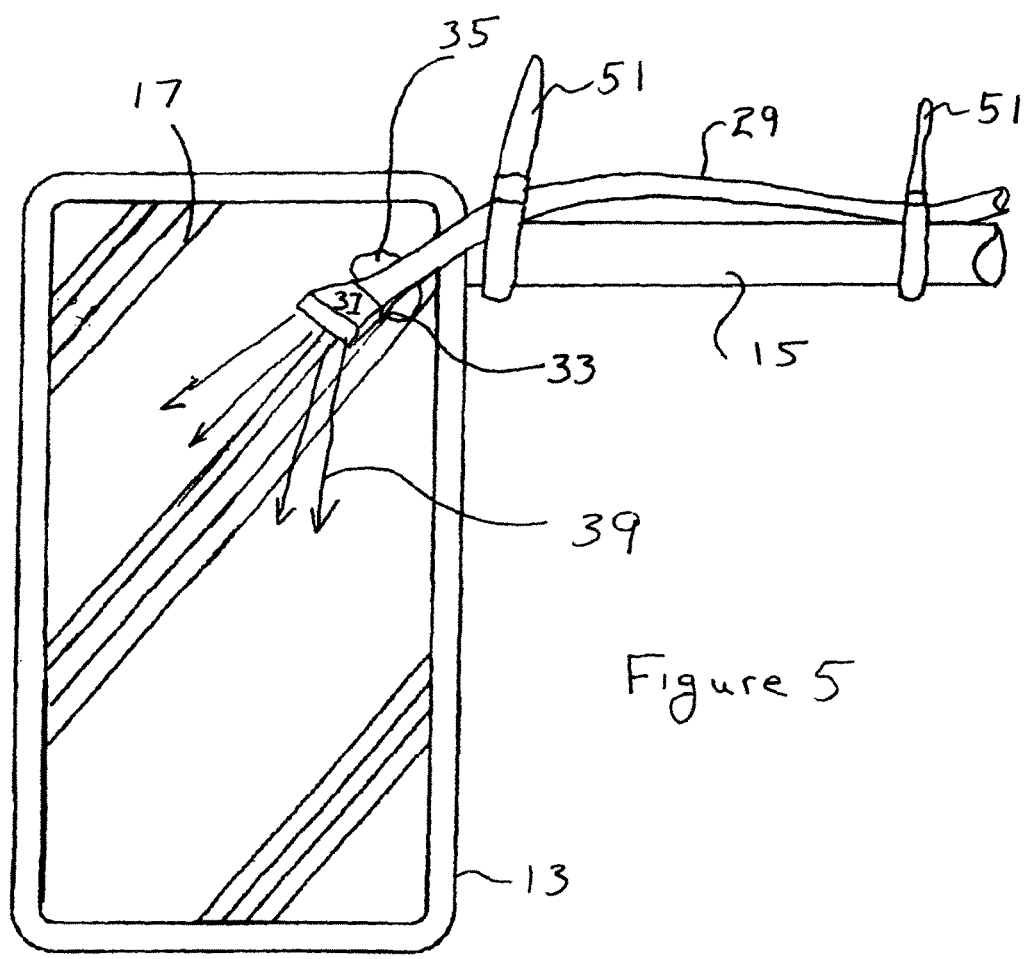
FIG. 5 is a planar view of the embodiment of FIG. 4.

Referring to FIG. 5, a detailed view of the arrangement for attaching the distal end 33, which includes nozzle 37, at the optical surface 17 of the side-view mirror 13 is illustrated. In this embodiment the conduit 29 is secured along support 15 using, for example, ties 51 or the like, although any suitable fastening arrangement can used, and the distal end 33. Including nozzle 37, of the conduit 29 is secured on the optical surface 17 of the mirror 13 using glue 35. The use of glue 35 permits the precise positioning of the nozzle 37 on the optical surface 17, preferably at a top portion of the side-view mirror 13 so that the blast 39 of pressurized air is directed generally downward and at a substantial portion of the optical surface 17 of the mirror 13. In cooperation with gravity, the blast 39 of air blows off water adhering to and obscuring the optical surface. The nozzle 37 facilitates a fanning out of the blast 39 of pressurized air to form a sheet of high velocity air flowing over the surface 17 and forcing adhering water to the edges of the optical surface 17 where it is carried away by the air through which the vehicle is moving.

Figure 6:
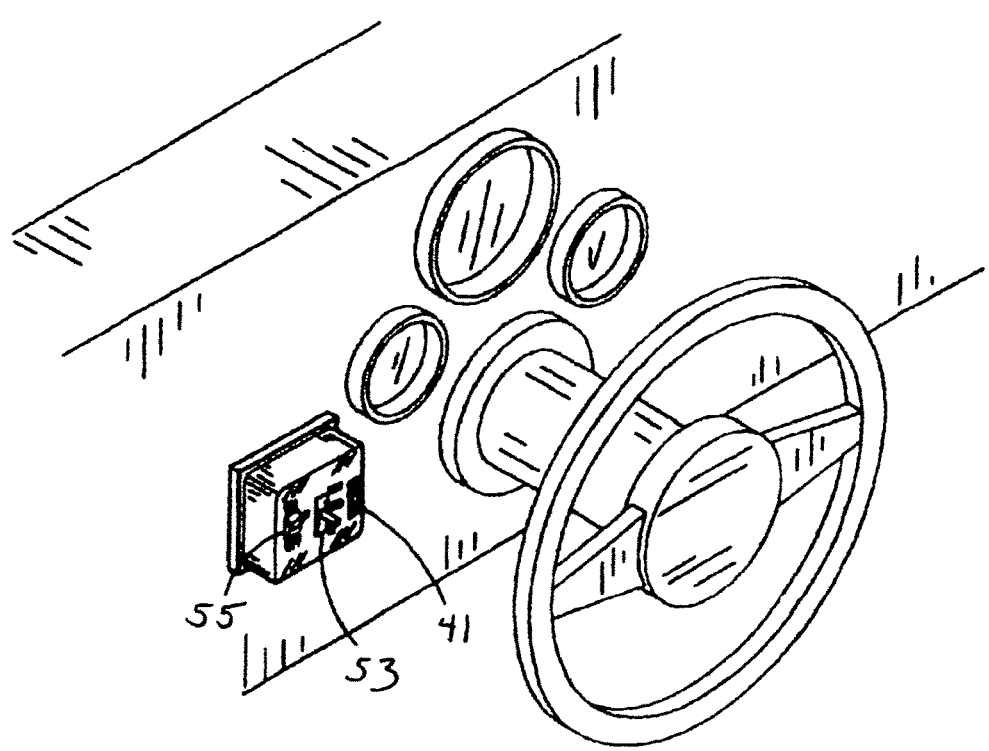
FIG. 6 is a perspective view of various embodiments of the switching mechanism of the present invention.

With particular reference to FIG. 6, the switching mechanism 41 is located in the cab of the vehicle 11 within easy reach from the driver's position. The switching mechanism 41 comprises a manual switch, such as a toggle switch 53 operated manually by the driver or it can be made to operate automatically by connecting the switching mechanism 41 to the windshield wiper switching mechanism 55 so that a blast of air to the optical surfaces of the side-view mirrors or vehicle mounted camera is provided periodically to the side-view mirrors, such as, for example, each time the windshield wipers cycle across the windshield. In addition, the switching mechanism can comprise a combination of both the manual toggle switch 53 and the automatic arrangement connected to the windshield wiper mechanism so that if an immediate clearing of the optical surfaces of the side-view mirror 13 or vehicle mounted camera 16 is necessary, the driver can toggle the toggle switch and send a blast of air to clean and clear these optical surfaces as much as needed.

Although the present invention has been described in terms of specific exemplary embodiments, it will be appreciated that various modifications and alterations might be made by those skilled in the art without departing from the spirit and scope of the invention as specified in the following claims.

What is claimed is:

1. An arrangement for clearing at least one optical surface of a vehicle of moisture, the vehicle including an existing source of compressed air, the arrangement comprising:
   a valve having an input port for connecting to the existing source of compressed air and an output port, the valve being moveable between open and closed positions to control the flow of compressed air from the existing source of compressed air to the output port of the valve to provide a blast of pressurized air;
   a conduit having a proximal end connected to the output post of the valve and a distal end located at the optical surface for conducting the blast of compressed air from the output port of the valve to the optical surface;
   a nozzle positioned adjacent to the optical surface, the nozzle having an outlet shaped and positioned for fanning out the blast of compressed air from the conduit downwardly and over a substantial portion of the optical surface;
   a fastener configured to fasten the nozzle adjacent to the optical surface; and
   a switching mechanism for opening and closing the valve to provide the blast of compressed air onto the optical surface to remove any obstructive moisture adhering to the surface, wherein the vehicle has windshield wipers, separated from the optical surface, that turn on and off and wherein the valve switching mechanism is automatically operated to periodically provide blasts of air to the optical surface while the wipers are turned on, wherein the at least one optical surface comprises a lens of a camera for monitoring the area behind the vehicle, or a transparent lens cover of a camera for monitoring the area behind the vehicle.

2. An arrangement according to claim 1, wherein the at least one optical surface comprises a plurality of optical surfaces additionally including one of: a rear window, or an exterior mounted rear-view mirror.

3. An arrangement according to claim 1, wherein the at least one optical surface comprises a plurality of optical surfaces of the vehicle and the valve has a plurality of output ports for selectively controlling the blast of compressed air to at least one of the plurality of optical surfaces.

4. An arrangement according to claim 1, wherein the switching mechanism is located within reach of a driver location of the vehicle.

5. An arrangement according to claim 1, wherein the fastener fastens a distal end of the conduit and the nozzle at a top end of the optical surface.

6. An arrangement according to claim 1, wherein the fastener comprises tape securing the distal end of the conduit at the optical surface and gluing the nozzle to the optical surface.

7. An arrangement according to claim 1, wherein the optical surface has edges and the nozzle is positioned at a top portion of the optical surface for issuing a generally downward directed sheet of pressurized air to blast any unwanted moisture adhering to the surface towards the edges of the surface.

8. A kit for retrofitting a vehicle with an arrangement of clearing at least one optical surface on a vehicle of moisture, the kit comprising:
   an independent source of compressed air;
   a valve having an input port for connection to the independent source of compressed air and an output port, the valve being movable between open and closed positions to provide a blast of compressed air from the source of compressed air to the output port of the valve;
   a conduit configured to connect to the output port of the valve for conducting a blast of compressed air from the output port of the valve to a nozzle to be attached directly onto the optical surface, the nozzle having an outlet shaped for fanning out the compressed air substantially downward and onto and over substantially an entire width of the optical surface;
   a fastener configured to fasten the nozzle onto the optical surface with the outlet positioned downwardly; and
   a switching mechanism for opening and closing the valve to provide the blast of compressed air downwardly over the optical surface to remove any obstructive moisture adhering to the optical surface, wherein the vehicle has windshield wipers, separated from the optical surface, that turn on and provide blasts of air to the optical surface while the wipers are turned on, wherein the at least one optical surface comprises a lens of a camera for monitoring the area behind the vehicle, or a transparent lens cover of a camera for monitoring the area behind the vehicle.

9. A kit according to claim 8, wherein the fastener comprises tape for taping the distal end of the conduit at the optical surface and glue for gluing the nozzle to the optical surface.

10. A kit according to claim 8, wherein the at least one optical surface comprises a plurality of optical surfaces additionally including one of: a rear window, or an exterior mounted rear-view mirror.

11. A water-removal arrangement for an optical surface of a back-up camera of a vehicle, the vehicle having an existing source of compressed air, the arrangement comprising:
   a valve having an input port connected to the existing source of compressed air and an output port, the valve being movable between open and closed positions to control a flow of compressed air from the existing source of compressed air to the output port of the valve;
   a conduit having a proximal end connected to the output port of the valve and a distal end located at the optical surface of the back-up camera for conducting the compressed air from the output port of the valve to the back-up camera;
   a fastener configured to fasten the distal end of the conduit to the optical surface of the back-up camera so that the compressed air flows down the optical surface;
   a nozzle on the distal end of the conduit and precisely positioned on the optical surface of the back-up camera for spreading the compressed air issued from the distal end of the conduit substantially over an entire width of the optical surface of the back-up camera; and
   a switching mechanism for opening and closing the valve to provide a blast of compressed air at the optical surface of the back-up camera to Clearwater adhering to the optical surface, wherein the valve switching mechanism is located within easy reach of a driver location of the vehicle, wherein the valve switching mechanism is manually operated by a driver of the vehicle, and wherein the vehicle has windshield wipers that turn on and off and wherein the valve switching mechanism is automatically operated to periodically provide blasts of air to the back-up camera while the wipers are turned on.

12. An arrangement according to claim 11, wherein the vehicle has a pair of back-up cameras and the valve has a pair of output ports each respectively connected to a conduit for conducting the compressed air to one of the back-up cameras of the vehicle.

13. An arrangement according to claim 11, wherein the conduit comprises flexible tubing.

14. An arrangement according to claim 11, wherein the fastener fastens the distal end of the conduit at a top end of the back-up camera.

15. An arrangement according to claim 11, wherein the fastener is glue.

16. An arrangement according to claim 11, wherein the distal end of the conduit is positioned at a top portion of the back-up camera for issuing a generally downwardly directed sheet of compressed air from the top portion of the back-up camera over substantially the entire optical surface of the back-up camera to blow off any water adhering to the optical surface.

17. An arrangement according to claim 11, wherein the vehicle has a windshield wiper switching mechanism and the valve switching mechanism is connected to the windshield wiper switching mechanism.

18. An arrangement according to claim 17, wherein the valve switching mechanism is connected to the windshield wiper switching mechanism so that the valve is opened to provide the blast of compressed air at the optical surface of the back-up camera each time the windshield wipers cycle.

19. An arrangement according to claim 1, wherein the vehicle has a windshield wiper switching mechanism and the valve switching mechanism is connected to the windshield wiper switching mechanism.

20. An arrangement according to claim 19, wherein the valve switching mechanism is connected to the windshield wiper switching mechanism so that the valve is opened to provide the blast of compressed air at the optical surface each time the windshield wipers cycle.

* * * * *